(12) United States Patent
Wotton (10) Patent No.: US 10,582,958 B2
(45) Date of Patent: Mar. 10, 2020

(54) BONE FIXATION PLATE (71) Applicant: Harry Wotton, Woodstock, CT (US)

(72) Inventor: Harry Wotton, Woodstock, CT (US)

( * ) Notice: Subject to any disclaimer, the term of this patent is extended or adjusted under 35 U.S.C. 154(b) by 0 days.

(21) Appl. No.: 15/527,896

(22) PCT Filed: Nov. 18, 2015

(86) PCT No.: PCT/GB2015/053495
§ 371 (c)(1),
(2) Date: May 18, 2017

(87) PCT Pub. No.: WO2016/079504
PCT Pub. Date: May 26, 2016

(65) Prior Publication Data
US 2018/0325568 A1 Nov. 15, 2018

(30) Foreign Application Priority Data
Nov. 21, 2014 (GB) .................... 1420739.3

(51) Int. Cl.
| | | |
|---|---|---|
| *A61B 17/80* | (2006.01) | |
| *A61D 1/00* | (2006.01) | |
| *A61F 2/28* | (2006.01) | |
| A61B 17/00 | (2006.01) | |
| A61F 2/30 | (2006.01) | |

(52) U.S. Cl.
CPC ...... *A61B 17/8057* (2013.01); *A61B 17/8052* (2013.01); *A61B 17/8061* (2013.01); *A61D 1/00* (2013.01); *A61F 2/28* (2013.01); *A61B 2017/00946* (2013.01); *A61F 2002/2892* (2013.01); *A61F 2002/30703* (2013.01)

(58) Field of Classification Search
CPC ............ A61B 17/8057; A61B 17/8047; A61B 17/8052; A61B 17/8028; A61B 17/8095
See application file for complete search history.

(56) References Cited

U.S. PATENT DOCUMENTS

| | | |
|---|---|---|
| 4,867,144 A | 9/1989 | Karas et al. |
| 4,988,350 A | 1/1991 | Herzberg |
| 5,304,180 A | 4/1994 | Slocum |

(Continued)

FOREIGN PATENT DOCUMENTS

| | | | |
|---|---|---|---|
| FR | 2965470 A1 | 4/2012 | |
| FR | 3003155 A1 | 9/2014 | |

(Continued)

OTHER PUBLICATIONS

International Search Report from corresponding International Patent Application No. PCT/GB2015/053495, dated Feb. 17, 2016.

(Continued)

*Primary Examiner* — Andrew Yang
(74) *Attorney, Agent, or Firm* — Kusner & Jaffe (57) ABSTRACT

A fixation plate comprising a head section for fixation to a first bone segment; a leg section extending from said head section for fixation to a second bone segment; wherein at least one of said head section and said leg section comprises at least one aperture configured to receive a screw for said fixation, and wherein said aperture is configured to receive said screw such that said screw can be inserted at varying angles.

18 Claims, 5 Drawing Sheets

(56) References Cited

U.S. PATENT DOCUMENTS

| | | | |
|---|---|---|---|
| 6,221,075 B1* | 4/2001 | Tormala | A61B 17/80 606/283 |
| 6,235,032 B1* | 5/2001 | Link | A61B 17/8061 606/280 |
| 7,722,653 B2* | 5/2010 | Young | A61B 17/8014 606/280 |
| 8,317,843 B2* | 11/2012 | Pisharodi | A61B 17/8052 606/281 |
| 8,870,931 B2* | 10/2014 | Dahners | A61B 17/8047 606/289 |
| 2006/0212035 A1 | 9/2006 | Wooton, III | |
| 2006/0264949 A1 | 11/2006 | Kohut et al. | |
| 2007/0088360 A1 | 4/2007 | Orbay et al. | |
| 2009/0234359 A1 | 9/2009 | Onoue et al. | |
| 2010/0057132 A1 | 3/2010 | Graham et al. | |
| 2011/0264149 A1* | 10/2011 | Pappalardo | A61B 17/8019 606/286 |
| 2013/0103104 A1* | 4/2013 | Krupp | A61B 17/808 606/86 B |
| 2014/0277178 A1 | 9/2014 | O'Kane et al. | |
| 2015/0327899 A1* | 11/2015 | Early | A61B 17/80 606/280 |

FOREIGN PATENT DOCUMENTS

| | | |
|---|---|---|
| GB | 2484007 A | 3/2012 |
| KR | 10-0706290 B1 | 4/2007 |
| WO | WO 2005/046494 A1 | 5/2005 |
| WO | WO 2014/027160 A1 | 2/2014 |

OTHER PUBLICATIONS

Search Report issued in connection with GB 1420739.3, dated Apr. 20, 2015.

http://web.archive.org/web/20140901231635/http//everost.com/products-tplo.html.

http://web.archive.org/web/20140901025732/http//everost.com/products-tplo-freedom-lock.html.

* cited by examiner

BONE FIXATION PLATE

RELATED APPLICATIONS

The present application is a U.S. National Stage Application of International Application No. PCT/GB2015/053495, filed Nov. 18, 2015, which claims priority from United Kingdom Patent Application No. 1420739.3, filed Nov. 21, 2014, said patent applications hereby fully incorporated herein by reference.

FIELD OF THE INVENTION

The present invention relates to a bone fixation plate. The bone fixation plates described herein may be used for the fixation of bones in animals, including canines.

BACKGROUND OF THE INVENTION

Bone fixation plates may be used in tibial osteotomy and other procedures to secure two bone segments together. In a tibial osteotomy, for example, a curvilinear cut is made in the canine proximal tibia to separate the metaphysis from the proximal tibia. Next, the metaphysis is rotated to level the tibial plateau. Finally, the metaphysis is fixed to the proximal tibia by a fixation plate. See U.S. Pat. No. 5,304,180.

US 2006/0212035 A1 describes a bone fixation plate that includes a broad triangular portion to be fixed to the metaphysis of the tibia and a narrower leg section to be fixed to diaphysis of the tibia. There are three bone screw holes in the triangular portion and three bone screw holes in the leg section.

There have been reports of increased tumor occurrences when relatively thick (approximately 5 mm) fixation plates cast from surgical grade stainless steel and are used. See "Metallurgical Evaluation of the Slocum TPLO Plate", Boudrieau et al., paper presented at the 32nd Annual Conference of the Veterinary Orthopedic Society, Mar. 5-12, 2005.

U.S. Pat. Nos. 4,867,144 and 4,988,350 disclose other configurations for bone fixation plates. In many fixation plates, there is a fairly sharp transition between the wide and narrow sections of the fixation plate resulting in a possible weak stress zone subject to breakage. U.S. 2006/0212035 A1 describes a bone fixation plate which has a head section that gradually tapers to smoothly cojoin with the leg section and wherein the expanse of the leg section continues to taper to a distal rounded end of the leg section.

SUMMARY OF THE INVENTION

In one aspect, there is provided a fixation plate comprising a head section for fixation to a first bone segment, a leg section extending from said head section for fixation to a second bone segment, wherein at least one of said head section and said leg section comprises at least one aperture configured to receive a screw for said fixation, and wherein said aperture is configured to receive said screw such that said screw can be inserted at varying angles.

Preferably, the aperture is a threadless aperture and the aperture is made from a material that deforms to form a screw thread within the aperture upon insertion of a threaded screw into the threadless aperture. Even more preferably, the material is a polymer.

Preferably, the aperture includes a plurality of interrupted threads. The plate may be made from stainless steel or titanium.

In another aspect, there is provided a kit comprising a fixation plate comprising a head section for fixation to a first bone segment, a leg section extending from said head section for fixation to a second bone segment, wherein at least one of said head section and said leg section comprises at least one aperture configured to receive a screw for said fixation; and a screw having a plurality of interrupted threads. Preferably, the interrupts are not equidistant apart.

In another aspect, the present invention is directed to a fixation plate comprising a head section for fixation to a first bone segment, a leg section extending from the head section for fixation to a second bone segment, wherein at least one of the head section and the leg section comprises at least one aperture configured to receive a screw for the fixation, wherein the aperture does not comprise a screw thread.

Preferably, the inner surface of at least one of the apertures is made from a material that deforms to form a screw thread within the aperture upon insertion of a threaded screw into the threadless aperture.

In another aspect, there is provided a fixation plate comprising a head section for fixation to a first bone segment, a leg section extending from the head section for fixation to a second bone segment, wherein at least one of the head section and the leg section comprises at least one position indicator provided thereon, the position indicator being made from a material that is configured to receive a screw for the fixation.

Preferably, the at least one position indicator is made from a material that deforms to form an aperture comprising an internal screw thread within the plate upon insertion of a threaded screw into the plate at the location of the position indicator.

Preferably, the materials described above comprise polymer.

In another aspect, the present invention is directed to a fixation plate comprising a head section for fixation to a first bone segment, a leg section for fixation to a second bone segment, the head section extending from a first end of the fixation plate to the leg section, and the leg section extending from the head section to a second end of the fixation plate, the leg section having lateral sides extending between the head section and the second end of the fixation plate and wherein one of the lateral sides comprises a protrusion that protrudes laterally away from the leg section of the plate.

Preferably, the leg section extends along a first longitudinal axis L1 between the head section and the second end of the fixation plate and wherein the lateral protrusion extends along a second axis L2 that intersects the axis L1.

In one embodiment, the second axis L2 intersects said first axis L1 at an angle of between 30-60 degrees, 40-50 degrees, and preferably 45 degrees.

Preferably, the leg section comprises at least one aperture configured for receiving a screw for fixation of the plate to the second bone segment and wherein the aperture has a center that is aligned with said first axis L1. In another embodiment, the fixation plate further comprises a second aperture that has a center that is aligned with said first axis L1. Preferably, the aperture is circular. In another embodiment, the aperture may comprise a beveled edge.

Preferably, the leg section comprises a third aperture that comprises two overlapping circular sections to provide the third aperture with an internal shape of the figure of 8.

Preferably, the fixation plate if this aspect may further comprise an aperture in the lateral protrusion of the leg implant. In a preferred embodiment, the aperture in the lateral protrusion has a center that is aligned with the second axis L2. In a further preferred embodiment, the aperture in the lateral protrusion is elongated along the second axis L2.

In another aspect, the present invention is directed to a fixation plate comprising a head section for fixation to a first bone segment a leg section extending from the head section for fixation to a second bone segment wherein at least one of the head section and the leg section comprises at least one aperture configured to receive a screw for the fixation.

Preferably, a screw thread is preformed in the at least one aperture. In another embodiment of this aspect, the plate is made from stainless steel.

In a preferred embodiment of all aspects above, the head section extends along an axis L3 from a first end of the head section to a second end of the head section that from which the leg section extends. Preferably, the head section comprises first and second apertures that each has a center point that is aligned with said axis L3. In a preferred embodiment, the axis L3 is parallel to the axis L1 and laterally offset to the axis L1.

In a preferred embodiment, the leg section extends in a plane P and wherein the head section extends away from the plane P. Preferably, the plate comprises a first side and an opposing second side and a sidewall having a thickness t1 there between and, preferably, the thickness is non-uniform across the plate.

In a preferred embodiment, the second side of the plate comprises a recessed channel. Preferably, in the area of the recessed channel the sidewall has a thickness t2 that is less than the thickness t1 of the plate.

In a preferred embodiment, the plate is made from a polymer, and, preferably, the polymer is bioabsorbable. In another embodiment, the plate comprises a blend of said polymer with an additive. In one embodiment, the additive comprises biphasic calcium phosphate, said biphasic calcium phosphate comprising 70% hydroxyapatite and 30% tricalcium phosphate, and a binding agent.

In another aspect, there is provided a kit having a fixation plate as described above and a screw configured to be screwed into an aperture so as to create a screw thread in the aperture.

BRIEF DESCRIPTION OF THE DRAWINGS

Various embodiments of the present invention will now be described, by way of example only, and with reference to the drawings, in which.

DETAILED DESCRIPTION

Figure 1:
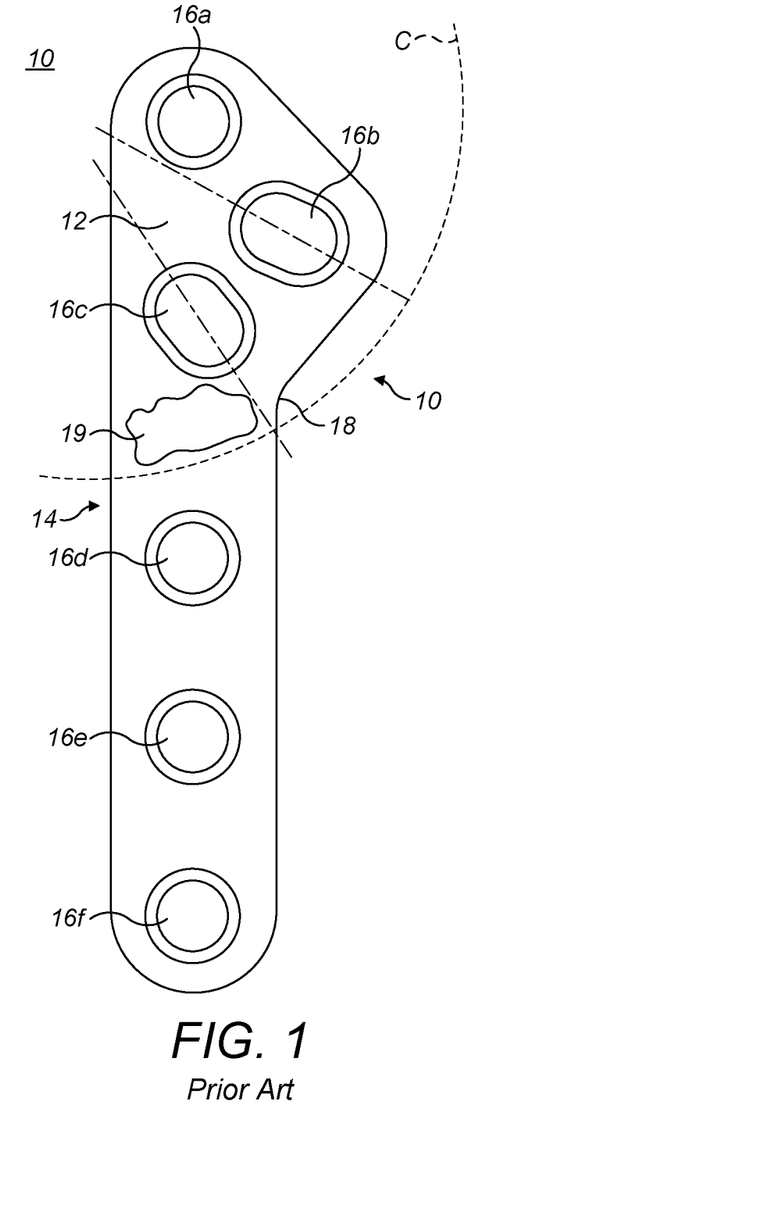
FIG. 1 is a schematic front view of a bone fixation plate in accordance with the prior art and as described in U.S. Pat. No. 5,304,180.

FIG. 1 is a schematic front view of a bone fixation plate in accordance with the prior art and as described and shown in U.S. Pat. No. 5,304,180.

The tibial osteotomy fixation plate 10 of U.S. Pat. No. 5,304,180 is shown spanning curvilinear cut C wherein triangular portion 12 is to be attached to the metaphysis and leg portion 14 is to be attached to the tibia using bone screws (not shown) seated in apertures 16a-f. Plate 10 is cast from surgical grade stainless steel and thus is relatively thick (approximately 5 mm) and possibly toxic. Also, the somewhat sharp transition at area 18 between triangular portion 12 and leg 14 results in a weak area in region 19.

In some embodiments, the fixation plate of the present invention may be machined out of surgical implant grade 316L stainless steel or titanium. In other embodiments, the plate may be made from a bioabsorbable blend of Poly Lacitdes specifically Poly L/D/L Lactide (PLDLA). In some embodiments, the implant may comprise the addition of further additives and in some embodiments may be a blend of PLDLA and biphasic calcium phosphate with a proprietary binding agent, with the inclusion of further additives, e.g. 60% PLDLA/40% biphasic calcium phosphate. The 40% biphasic calcium phosphate is 70% hydroxyapatite and 30% TCP. For example, in some embodiments, the blend of PLDLA may include TCP (tricalcium phosphate) which supports and stimulates bone growth. In other examples, bioglass may be added to increase the strength of the implant. In other embodiments, pharmaceuticals or other healing compounds may be added and used within the material. As the fixation plate implant is absorbed by the body the pharmaceutical will then slowly be released at the implant site. By using a bioabsorbable polymer, the implant may be at least partially absorbed into the body after the bone has healed. Such bioabsorbable polymers are also more biocompatible than metal implants and by using such materials the chance of infection is also reduced, because the surface of a bioabsorbable implant is constantly changing and so it is difficult for the bacteria to grow.

In the embodiments described herein, the screws that may be used with the fixation plate may be made from a polymer such as a bioabsorbable polymer, or may be made from a biocompatible metal, including examples such as titanium or stainless steel. Other biocompatible materials as are known in the art may also be used.

In some embodiments, the fixation plate may be made from a radiolucent material so that when x-rayed, only the bone growth would show up and not the implant itself. This would give the surgeon a clear and unobstructed view of the bone growth during healing.

Figure 2:
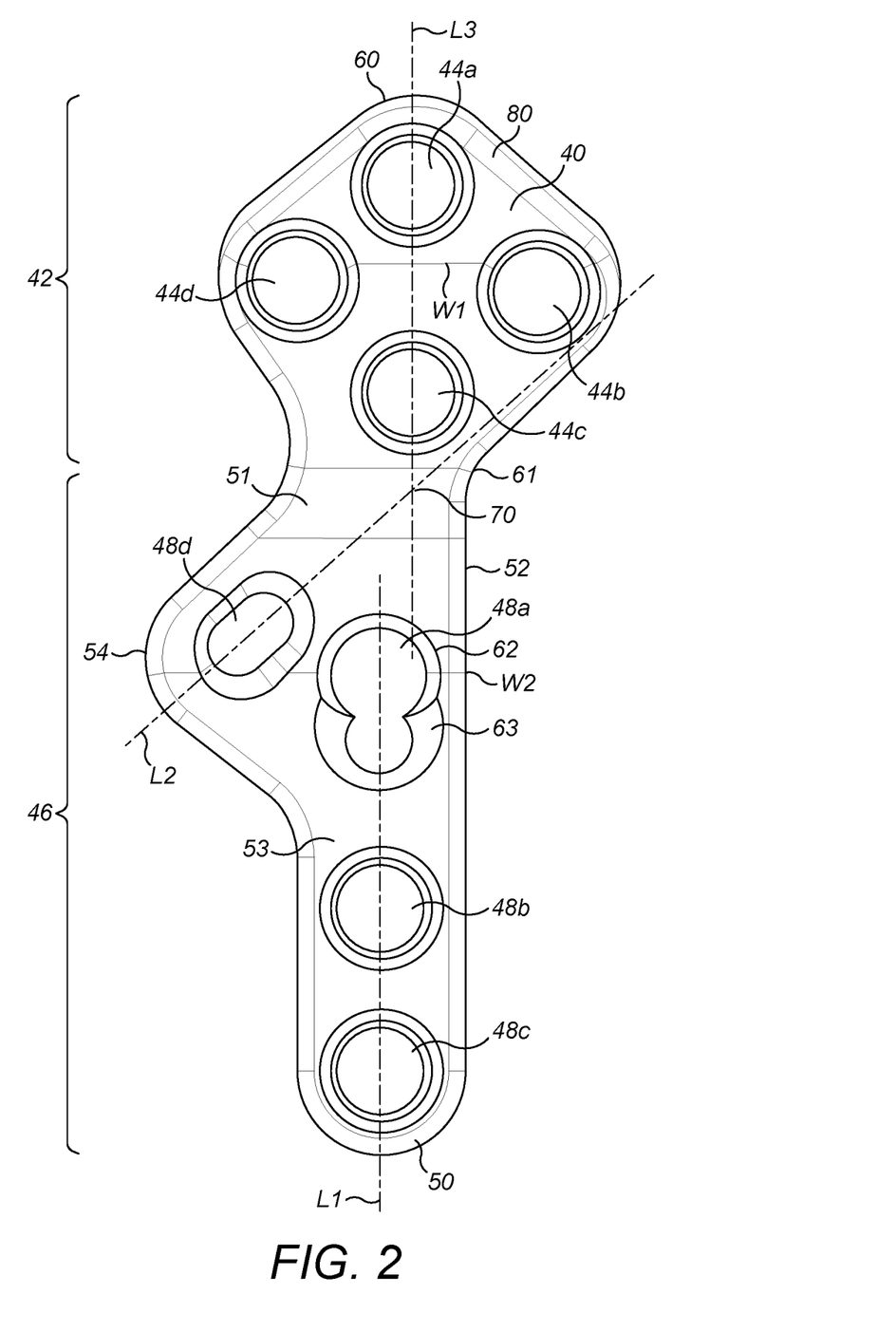
FIG. 2 is a schematic top view of one example of a bone fixation plate in accordance with the present invention.

One example of a fixation plate 40, in accordance with the present invention, is shown in FIG. 2 and includes two distinct sections, a head section 42 comprising apertures 44a, 44b, 44c and 44d for fixation to one bone segment (e.g. the medial segment), and a leg (or "tail") section 46, extending from the head section, the leg section 46 including apertures 48a, 48b, 48c and 48d for fixation to another bone segment, e.g. distal segment (diaphysis). The fixation plate extends between a first, proximal end 60 and a second, distal end 50.

The uniquely shaped head section 42 of the present invention as described below allows the plate to be placed in multiple locations on the bone to get the desired fixation.

The head section 42 may be described as being generally square, or diamond shaped, with rounded corner edges and extends from the first end 60 of the plate to a second end 61 of the head section 42. In particular, the head section 42 extends from a first corner and first end 60 of the square or diamond at the proximal end 60 of the plate in the direction of the leg section as can be seen in FIG. 2. The head section 42 has a width w1 that initially increases with distance away from this first end 60 of the head section, in the direction of the leg section 46. The width w1 then reaches a maximum distance e.g. 18-25 mm at the approximate middle of the head section 42 (i.e. the middle of the square or diamond) before it begins to gradually decrease again in the direction of the second end 61 of the head section, as shown in FIG. 2. The head section 42 can be seen in FIG. 2 as gradually tapering at its second end 61 to smoothly join a first end 51 of the leg section 46, as shown in FIG. 2, from where the leg section begins.

The leg section of the fixation plate also has and extends between a first end 51 (which is joined to the second end of the head section 42) and a second end 50, which corresponds to the second, distal end 50 of the plate itself. The leg section can be seen as being asymmetrical in that, as it extends from the head section towards the distal end, it has a lateral protrusion 54 on one side 53, whereas the other lateral side 52 does not have this protrusion. For example, one lateral side 52 of the leg section (shown as being on the right hand side of FIG. 2) extends linearly from the first end 51 of the leg section 46 (and also away from the head section 42) in the direction of the second, distal end 50 of the leg section and terminates by smoothly tapering to form the distal rounded end 50 of the fixation plate. The other opposing, lateral side 53 of the leg section does not extend linearly from the head section, but instead comprises a protrusion 54 that extends laterally away from the first end 51 of the main body of the leg section 46 as shown in FIG. 2.

This protrusion therefore helps to provide the bone fixation plate 40 with an anatomically pre-contoured shape, to thereby closely fit the bone surface to which it is applied and to reduce the amount of bending prior to fixation. This detail goes towards the center of the tibia and allows the surgeon to take advantage of a lot of bone stock when placing that screw.

As mentioned above, and as can be seen in FIG. 2, the bone fixation plate has a first end 60 and an opposite second end 50. A first longitudinal axis L1 extends from the center of the distal second end 50 of the fixation plate and along the length of the main body of the leg section 46. The leg section further comprises means for fixing the leg section to a bone. In the example shown in FIG. 2, the means for fixing the plate to the bone comprise apertures that are configured to receive locking or fixing means such as screws. The example shown in FIG. 2 comprises four apertures in the leg section. Two of the apertures 48b and 48c of the leg section 46 may be generally circular in shape and can be seen in FIG. 2 as being positioned so that so that the center points of these apertures both lie on this first longitudinal axis L1. All of the apertures can accept a locking screw or a standard non locking screw.

As can be seen in FIG. 2, a third aperture 48a is positioned closer to the head section than the apertures 48b and 48c. This aperture 48a of the leg section of the implant may be shaped so as to comprise a first circular section 62 and an overlapping second circular section 63. The second section 63 in this example is smaller than the first section 62 to facilitate use with a locking screw of a non-locking screw. The first, larger section is for a locking screw as, generally, locking screws have a larger head; the smaller second section is for a standard non-locking screw which has a smaller head. The second section is closest to the aperture 48b. Both sections 62 and 63 comprise circular apertures that overlap to result in the overall aperture 48a having an elongated shape that comprises an aperture having a figure of 8 internal shape, as shown in FIG. 2. This feature of the invention provides a "combination" aperture which may be used for either compression, or for locking/fixing, but not both at the same time, as described below. This feature also allows a screw to be placed more cranially which is central to the long axis of the tibia and a much better place to put a screw. The compression aperture in this section is at 45 degrees to the long axis of the plate so that compression can be put on the cut at two locations 45 degrees from each other. This gives more uniform compression across the radial cut. The center point of this combination aperture 48a is also aligned with the axis L1 and the two circular sections may be overlapped so that the overall aperture is therefore elongated along the axis L1, as shown in FIG. 2.

The minimum and maximum spacing between any two apertures 48a-48c in the main body of the leg section 46 may be, respectively, 7 mm and 12 mm.

The fourth aperture 48d of the leg section 46 of the plate is not aligned on the same longitudinal axis L1 as the other apertures of the leg section but instead is offset laterally to the main body of the leg section and the axis L1 as shown in FIG. 2. Specifically, the fourth aperture 48d of the leg section is positioned within the lateral protrusion 54, as described above. This laterally offset protrusion and therefore aperture 48d of the leg section is correctly placed to take advantage of a large portion of bone on the medial side of the bone to which the plate is being fixed. This aperture is offset to the other holes in the leg section, or "tail" of the implant. All other implants used in this procedure up until now only have the holes in the leg section aligned. Many times, however, the screws are placed and they are too close to the caudal aspect of the tibia with a concern that they might fracture out.

The lateral protrusion 54 extends away from the main body of the leg section along a second axis L2, as shown in FIG. 2. The fourth aperture 48d of the leg section 46 may be circular but in some embodiments may be elongated (as shown in FIG. 2) with the elongation also extending along a second axis L2. This second axis L2 extends at an angle to said first axis L1 and so that it intersects the first axis L1 at point 70 at an angle of between 30-60 degrees, 40-50 degrees, and preferably 45 degrees. In some embodiments, the fourth, elongated aperture 48d of the leg section of the plate may have at least one beveled end and/or beveled sides.

Circular apertures 48a-c in leg section 46 may also be beveled evenly around their circumferences. For strength, the minimum spacing between any two adjacent apertures in head section 42 may be 8 mm.

As can also be seen in FIG. 2, the head section 42 also has means for fixing the plate to a bone, which comprise apertures 44a-44c that are configured to receive fixing, or locking means, such as screws. Although the centers of the apertures 48a, 48b and 48c of the leg section 46 are aligned with each other on the first axis L1, their centers are not aligned with the center points of the apertures 44a, 44b, 44c and 44d of the head section. This offset puts the tail more cranial and closer to the long axis of the tibia. This allows the surgeon to place the plate as caudal as possible above the cut at the same time keeping the tail more cranial below the cut.

The center points of two of the apertures 44a and 44c of the head section that are closest to the first 60 and second end 61 of the head section are aligned on a further longitudinal axis L3 that is parallel to the axis L1, but which is slightly offset laterally in the opposite direction to the lateral protrusion 54 by e.g. 1-3 mm. This longitudinal axis L3 extends from the furthermost tip 60 of the first end of the fixation plate in the direction of the leg section. The center points of the apertures 44b and 44d which are at the widest parts of the head section are aligned on a fourth axis L4 which is perpendicular to both L1 and L3.

The center axis L3 of the apertures in the head section of the plate converge and would intersect at approximately 70 mm away. This ensures that the screw ends do not collide with any other screw end inside the bone or 2-5 mm outside the far side of the bone. If they were to collide in the bone they would not be able to be fully seated. The converging apertures increase the holding power of the implant so that if the implant was pulled off the bone, the material between the screws would need to break out, which would require more force than is possible to apply. Because the screw heads lock into the plate they cannot change their angle in the plate once fully seated. Standard non locking screws can change their angle if a load was applied to the implant (because they do not lock). Therefore, when using locking screws that have their heads fixed inside the plate, the loads required to get the plate to be pulled off the bone are significantly higher.

All of the apertures of the fixation plates described herein, except for the elongated aperture 48d in the protruding part of the leg section of the plate, may be used for fixing or locking the implant into position on the bone. The aperture 48d in the protruding section of the leg section, however, is intended to be used for compression.

Compression may be necessary or useful in some cases to push the two segments of bone together.

The aperture 48a of the leg section is a combination aperture in that it may be used for either locking (e.g. when the screw is inserted into the section 63), or for compression (when the screw is inserted into the section 62). Due to the fact that these individual circular sections overlap to form one elongated aperture makes it is impossible for the surgeon to insert both a locking and compression screw into this location at the same time. By applying compression along two axes that are 45 degrees apart, a more uniform compression is provided across the entire cut line. The aperture combining a locking and a non-locking screw allows the surgeon to choose to apply more compression or not.

In some embodiments of the invention, the aperture 48d provided in the lateral protrusion of the leg section may be angled so that compression is applied at a different angle than compression applied via section 62 of the aperture 48a. This gives a more uniform compression across the cut in the bone than if just one point of compression is used.

The fixation plates described herein have a first surface 80 which is the uppermost surface in use, and an opposing surface 81 which is generally facing the bone and so in contact with the bone when in use (i.e. fixed in place on the bone). A side wall 82 extends there between which dictates the thickness t1 of the implant. Some examples of plate thickness are set out in the table below.

| Plate size/dim | Thickness | Length | Width 1 | Width 2 |
| --- | --- | --- | --- | --- |
| 2.4 mm | 2.5 | 30 | 15 | 17 |
| 2.7 mm | 3.0 | 35 | 20 | 22 |
| 3.5 mm | 3.5 | 46.5 | 24 | 27 |
| 3.5 mm big | 4.0 | 80.00 | 25 | 28 |

Figure 3:
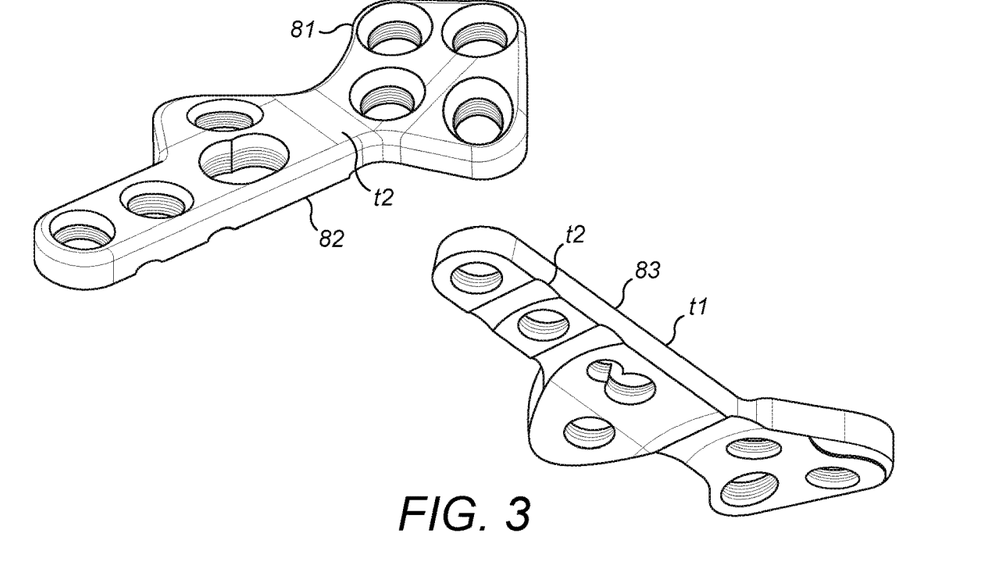
FIG. 3 shows two bottom views of a bone fixation plate in accordance with the present invention, showing the underside of the plate that is to be affixed to the bone.

In any of the embodiments described herein, the fixation implant may further comprise sections of reduced thickness t2. As can be seen in FIG. 3, this may be achieved by providing recessed channels 83 or scollops in one of the sides 80, 81 of the implant. The recessed channels are preferably provided in the second, underside 81 of the fixation plate (i.e. that which is facing the bone when the implant is attached thereto). In some examples, these recessed channels 83 in the underside 81 of the implant may extend all the way across the entire width of the base and/or leg section. For example, the recessed channel(s) may extend from a first lateral side 52 of the leg section of the implant to the second lateral side 53 of the leg section of the implant.

An advantage of providing these recessed channels 83 on the underside 81 of the implant is that it helps to reduce the amount of contact that the underside of the implant has with the bone when the plate is fixed in place. A further advantage of the fixation plate having these recessed channels 83 is that any bending forces that may be being applied to the implant would be concentrated at these areas of reduced thickness, instead of being concentrated in areas of the implant that would normally be subject to bending force, such as at the apertures containing the locking screws. This helps to reduce loosening or possible fracture of the screws and/or apertures. The recessed channels under the plate are placed between the apertures so that if the plate is further contoured all bending will occur there instead of through the screw holes.

Figure 4:
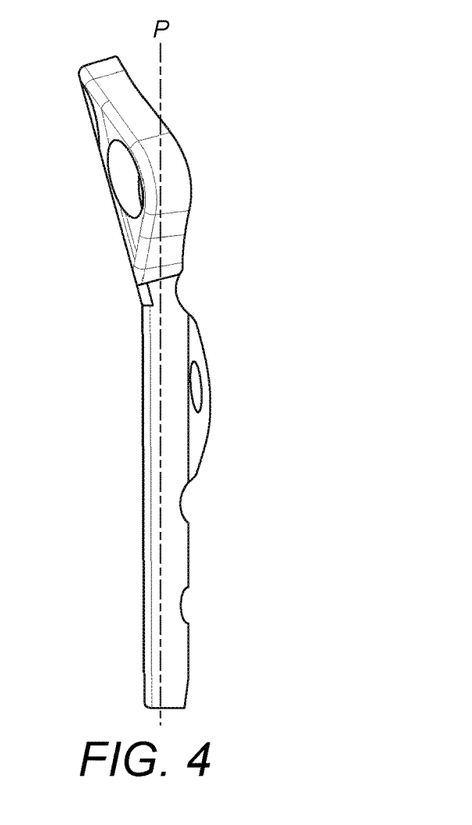
FIG. 4 shows a side cross sectional view of a bone fixation plate in accordance with the present invention.

The implants described herein may also be shaped so as to have a non-uniform cross-sectional profile, as shown in FIG. 4. For example, in some embodiments, the main body of the leg section of the implant (i.e. containing the apertures 48a-48c) may have a generally uniform linear cross section or profile that extends in a first plane P. In some embodiments, however, the head section 42 may extend away from this plane at an angle such as shown in FIG. 4. In FIG. 4 the head section extends in the upper direction (e.g. away from the bone) away from the leg section at an angle of 15 degrees to the plane P of the leg section 46, however, other angles within the range of e.g. 12-20 degrees may also be used.

Figure 5:
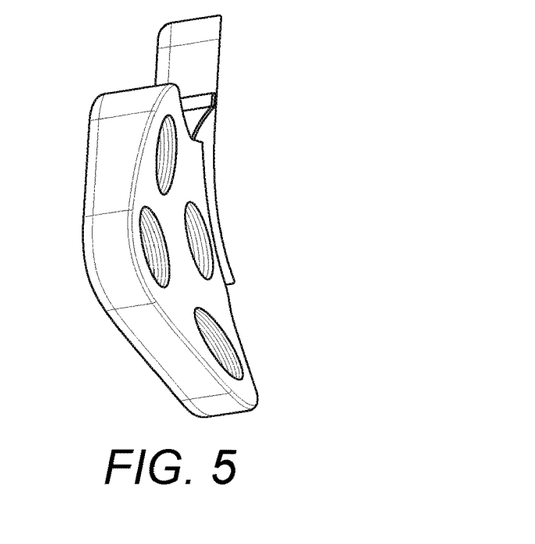
FIG. 5 shows a cross sectional view of the head section of a fixation plate, showing the concave underside of the head section.

The upper 80 and lower surface 81 of the head section 42 may also be curved, so that the upper surface 80 of the head section is convex whereas the lower surface 81 of the head section is concave, as shown in FIG. 5. Angles of curvature may be in the range of 18-28 mm depending on the size plate and the size patient. Due to fact that the head section has a curved profile with a convex upper surface and concave lower surface, the angles of the apertures 44a-44c in the head section of the plate may be set at particular angles that make it then impossible for the surgeon to place a screw into the aperture that would enter the joint. For example, the aperture angles may be 94 degrees for aperture 44a, 86 degrees for aperture 44b and 82 degrees for aperture 44c.

The profile of the protruding section 54 of the leg section may also extend and curve away from this plane P of the leg section as shown in FIG. 4. In particular, the protruding section 54 of the leg section may extend away from the plane P at an angle of 18-28 mm in the opposite direction to the head section, i.e. in the downward direction, towards the bone.

Figure 6:
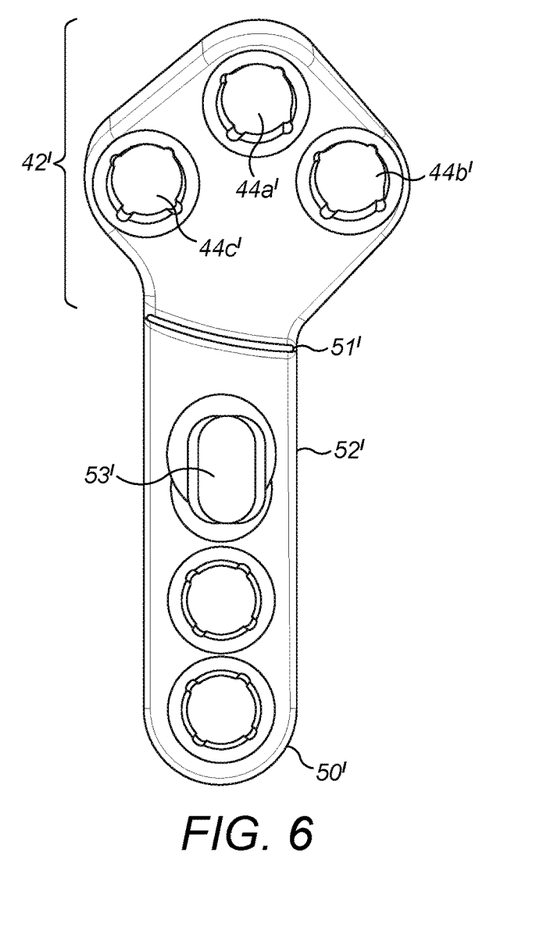
FIG. 6 shows a schematic top view of another example of a bone fixation plate in accordance with the present invention.
Figure 7:
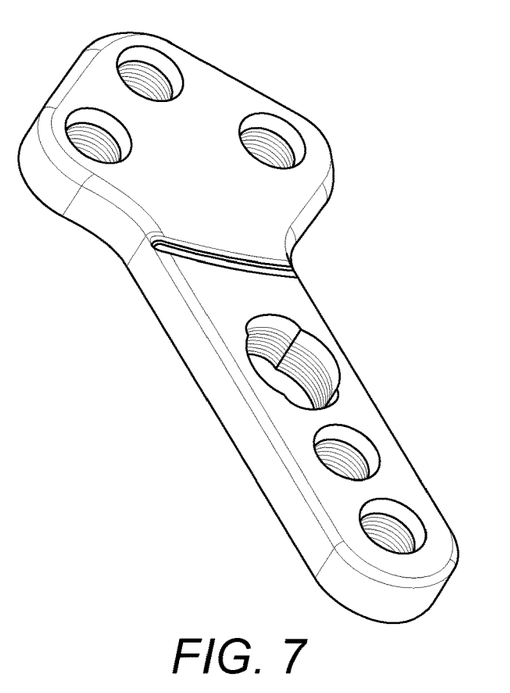
FIG. 7 shows a bottom view of the bone fixation plate of FIG. 6.
Figure 8:
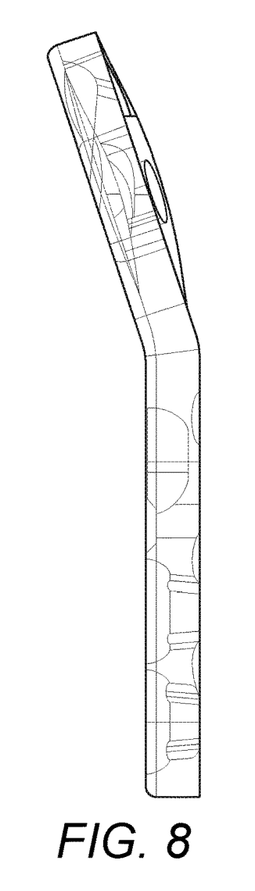
FIG. 8 shows a side cross sectional view of the bone fixation plate of FIG. 6 in accordance with the present invention.

FIGS. 6-8 show an alternative example to the fixation plate shown in FIGS. 2-5. FIG. 6 shows a top view of the fixation plate of this alternative example. The fixation plate has the same geometry as the fixation plate shown in FIGS. 2-5, but includes only three apertures 44a', 44b', 44d' in the head section 42'. Further, the fixation plate shown in FIGS. 6-8 does not include the protrusion portion 54 of FIGS. 2-5. In this example, the leg section can be seen as being symmetrical and the lateral sides 52' and 53' extend linearly from the first end 51' of the leg section (and also away from the head section 42') in the direction of the second, distal end 50'. In the example shown in FIGS. 6-8, the fixation plate may be made from a bioabsorbable material or a biocompatible metal, as described above in relation to FIGS. 2-5. In particular, it has been found that stainless steel has been an optimal material for the configuration in FIGS. 6-8.

Fixation plates such as these, having this non-uniform cross sectional profile more closely fit the contour of the bone to which they are affixed.

In embodiments wherein at least the apertures of the plate are made from a polymer, the apertures provided in the plates described herein may or may not be pre-threaded. A feature of some of the embodiments described herein is that the screws may be self-locking. In other words, in some embodiments, the apertures may comprise no threads and the screws may be provided with a screw thread which may then 'self-tap' into the apertures of the plate, thereby forming the screw threads in the polymer plate as they are inserted.

By providing a plate that has apertures containing no pre-formed screw threads, the plate thereby allows the surgeon to place the screw at whatever angle is necessary and/or appropriate for that particular application. Fixation plates having at least the inner surface of the apertures made from polymers such as poly lactides, specifically poly LDL lactides (PLDLA) allow for this 'self-tapping' feature, as the material is soft enough for the screw threads to be formed in the apertures upon insertion of a screw. In some embodiments, only the inner surface of the apertures need to be made from this deformable material. In other embodiments, the entire implant may be made from this material In contrast to this, fixation plates which have apertures that have threads pre-formed therein (e.g. for stainless steel or titanium plates) only allow for a screw to be inserted at a predetermined angle. In some cases, the predetermined angle is not necessarily the desired angle but the surgeon has no choice.

In some embodiments, wherein the plate is made from a material such as poly LDL lactides the fixation plate may contain no pre-formed apertures at all and the apertures as described above may be replaced by dents or markers on the plate to indicate to the surgeon where to insert the fixing or locking means (e.g. screws). The surgeon can then simply insert the screws into the bone plate at the appropriate place and appropriate angle. The advantages of the plate having only dents or markers are that the anatomy and surgeon's desire is often different than the basic anatomy. This would allow the surgeon to choose which angle is best and which direction to place the screw based on the patient's anatomy and fracture.

In some embodiments, wherein the fixation plate is made from a metal, specifically designed locking screws may be used in conjunction with the plate which allow the screws to be put into the plate with a plurality of degrees of freedom.

The holes in the plate are set at specific angles so that the surgeon can simply use those if that is desired. If the surgeon would then like to alter the angle, they can do so by a plurality of degrees in any direction. This is achieved by the screws comprising a plurality of interrupted threads. In one example, the screw comprises four sets of interrupted threads. This allows them to enter the apertures of the fixation plate by 15 degrees in any direction. By having the interrupts in the threads on the head, the screw thread has 4 starting positions (4 interrupts). With these multiple starting positions the screw threads can enter the plate at four different angles or locations allowing the screw to be placed at multiple angles.

In other embodiments, wherein the fixation plate is made from a metal, the apertures of the fixation plate may include a plurality of interrupted threads. The interrupted threads in the apertures allow for the surgeon to insert a screw into the plate with a plurality of degrees of freedom. In one example, the aperture comprises four sets of interrupted threads. This allows for the screw to enter the apertures of the fixation plate by 15 degrees in any direction. Preferably, the interrupts are not equidistant apart from each other.

The fixation plates are preferably made in four different sizes e.g. 2.4 mm, 2.7 mm, 3.5 mm and 3.5 mm big. Smaller sizes may also be used and mirror images of the plates may also be made (e.g. with the protrusion on the opposite to that shown in FIG. 2. The bone fixation plates described herein may, however, be scaled to fit any size dog by increasing the appropriate dimensions. Important dimensions would be overall length (L), thickness (T), width of head (W1) and width of head to laterally protruded section (W2). The sizes of each are based on historical data of patient size.

In some embodiments, the surface of the plates may comprise a mark which provides an indication of the preferred location of the implant over the bone. In some embodiments, wherein the plate is made from metal, the mark may be machined onto the surface of the plate.

Preferred materials for the plate are polymer, titanium and stainless steel. In an embodiment using stainless steel the plate may not have the protruding nose and may only have 3 holes in the base (head section) (44a, 44b and 44d) all the angles and geometry are the same as for the above example.

In a preferred embodiment, hole 44d is placed 2-3 mm higher than hole 44b. This is done to make sure the hole stays above the radial cut. The radial cut is going up so the hole needs to go up.

The fixation plates described herein therefore provide improved bone fixation and may be useful in tibial osteotomy and other procedures. The fixation plate of this invention is thinner, lightweight, and strong and is better contoured to the shape of the bone to which it is attached.

Any of the features of the implants described herein may be used in combination with any or all of the other features.

The invention claimed is:
1. A fixation plate, comprising:
a head section for fixation to a first bone segment;
a leg section extending from said head section for fixation to a second bone segment;
wherein at least one aperture is formed in at least one of said head section and said leg section, the aperture being configured to receive a screw for said fixation,
wherein said head section extends along a center head section axis (L3) extending from a first end of said head section through a center of the head section to a second end of said head section, wherein the leg section extends along a first longitudinal axis (L1) from the second end of said head section to a second end of the fixation plate, wherein said center head section axis (L3) is parallel to a first longitudinal axis (L1) that extends along the leg section between said head section and said second end of the fixation plate, said center head section axis (L3) being laterally offset to said first longitudinal axis (L1), wherein said head section comprises first and second head apertures that each have a center point through which said head section axis (L3) extends, wherein said leg section has lateral sides extending between said head section and said second end of the fixation plate, and wherein a protrusion that protrudes laterally away from said leg section of the plate is formed in one of said lateral sides, said protrusion being closer to the first longitudinal axis (L1) than the head section axis (L3).

2. The fixation plate of claim 1, wherein a screw thread is preformed in at least one of the head apertures.

3. The fixation plate of claim 1, wherein said leg section extends in a leg section plane (P), and
wherein said head section extends away from said leg section plane (P).

4. The fixation plate of claim 1, further comprising:
a first side;
a second side opposing said first side; and
a sidewall having a thickness (t1) between the first side and the opposing second side,
wherein said thickness (t1) is non-uniform across the plate.

5. The fixation plate of claim 4, wherein a recessed channel is formed in said second side, and
wherein, in an area of said recessed channel, the sidewall has a thickness (t2) that is less than said thickness (t1).

6. The fixation plate of claim 1, wherein said plate is made from a polymer that is bioabsorbable.

7. The fixation plate of claim 6, wherein said polymer is a part of a blend with an additive and a binding agent, the additive comprising biphasic calcium phosphate, said biphasic calcium phosphate being 70% hydroxyapatite and 30% tricalcium phosphate.

8. The fixation plate of claim 1,
wherein at least one first leg aperture and a second leg aperture are formed in the leg section, the first and second leg apertures being circular, the first leg aperture being configured to receive a screw for the fixation of said plate to said second bone segment, said first leg aperture having a first leg aperture center that is aligned with said first longitudinal axis (L1), said second leg aperture having a second leg aperture center that is aligned with said first longitudinal axis (L1), and
wherein a third leg aperture is formed in said leg section, said third leg aperture being formed of two overlapping circular sections.

9. The fixation plate of claim 8, wherein said third leg aperture has an internal shape of a figure eight.

10. The fixation plate of claim 8,
wherein said third leg aperture is positioned nearer to the head section than the first and second leg apertures.

11. The fixation plate of claim 8, wherein said third leg aperture has a third leg aperture center that is aligned with said first longitudinal axis (L1).

12. The fixation plate of claim 8, wherein a second overlapping circular section of the two overlapping circular sections is smaller than a first overlapping circular section of the two overlapping circular sections,
wherein the second overlapping circular section is closer to the first and second leg apertures than the first overlapping circular section.

13. The fixation plate of claim 8, wherein the first longitudinal axis (L1) extends through the first, second, and third leg aperture centers.

14. The fixation plate of claim 1,
wherein the lateral protrusion extends along a second axis (L2) that intersects the first longitudinal axis (L1), and
wherein a lateral protrusion aperture is formed in said lateral protrusion, said lateral protrusion aperture being elongated along said second axis (L2) in an oval shape and having a center aligned with said second axis (L2).

15. The fixation plate of claim 14, wherein said second axis (L2) intersects said first longitudinal axis (L1) at an angle in a range from 30° to 60°.

16. The fixation plate of claim 14, wherein the second axis (L2) extends through the lateral protrusion aperture center.

17. The fixation plate of claim 1, wherein the first and second head apertures are respectively closest of a plurality of head apertures of the head section to the first and second ends of the head section.

18. The fixation plate of claim 1, wherein said head section further comprises third and fourth head apertures that each have a center point through which an axis that is perpendicular to said head section axis (L3) extends.

* * * * *